United States Patent
Ueno et al.

(10) Patent No.: US 7,371,882 B2
(45) Date of Patent: May 13, 2008

(54) REACTOR FOR PRODUCING A NITRILE COMPOUND AND METHOD FOR OPERATING THE REACTOR

(75) Inventors: Shuichi Ueno, Niigata (JP); Takuji Shitara, Niigata (JP); Kenichi Nakamura, Niigata (JP); Fumisada Kosuge, Niigata (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 574 days.

(21) Appl. No.: 10/940,652

(22) Filed: Sep. 15, 2004

(65) Prior Publication Data
US 2005/0054855 A1 Mar. 10, 2005

Related U.S. Application Data

(62) Division of application No. 10/326,056, filed on Dec. 23, 2002, now abandoned.

(30) Foreign Application Priority Data

Dec. 25, 2001 (JP) ............................. 2001-391956
Dec. 25, 2001 (JP) ............................. 2001-391957

(51) Int. Cl.
*C07C 253/18* (2006.01)
(52) U.S. Cl. ...................................... 558/310; 558/327
(58) Field of Classification Search ............... 558/310, 558/327; 422/146, 198
See application file for complete search history.

(56) References Cited

U.S. PATENT DOCUMENTS 4,544,020 A 10/1985 Chrysostome et al.
5,700,432 A 12/1997 Tanaka et al.
6,110,440 A 8/2000 Ohta et al.
6,218,484 B1 4/2001 Brown et al.

FOREIGN PATENT DOCUMENTS

| EP | 1113001 A2 * | 7/2001 |
| FR | 2 034 019 | 12/1970 |
| WO | WO 99/15484 | 4/1999 |

OTHER PUBLICATIONS

Communication and European Search Report dated Aug. 11, 2004, for No. EP 02 02 8774.

* cited by examiner

*Primary Examiner*—James O. Wilson
*Assistant Examiner*—Ebenezer Sackey
(74) *Attorney, Agent, or Firm*—Antonelli, Terry, Stout & Kraus, LLP.

(57) ABSTRACT

A reactor for producing a nitrile compound from a carbon ring or heterocyclic compound having organic substituents by a gas phase reaction using a fluidized catalyst bed with ammonia and a gas containing oxygen. In a cylindrical fluidized catalyst bed having a diameter of 2.0 meters or greater, partial vaporization-type cooling tubes (the cooling medium is partially vaporized in the tubes) and complete vaporization-type cooling tubes (the cooling medium is completely vaporized in the cooling tubes) are disposed in a specific arrangement. Water containing ionic $SiO_2$ in 0.1 ppm or smaller and having an electric conductivity of 5 µS/cm or smaller is used as the cooling medium for the complete vaporization-type cooling tubes. The temperature of the reaction is easily stabilized and uniform distribution of temperature is obtained in the fluidized catalyst bed. Stable continuous operation is achieved for a long time in a commercial scale apparatus.

6 Claims, 3 Drawing Sheets

Figure 2

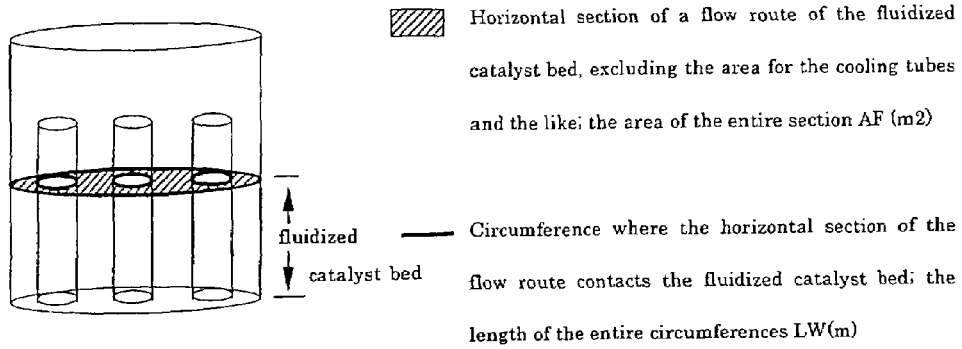

fluidized catalyst bed

▨ Horizontal section of a flow route of the fluidized catalyst bed, excluding the area for the cooling tubes and the like; the area of the entire section AF (m2)

— Circumference where the horizontal section of the flow route contacts the fluidized catalyst bed; the length of the entire circumferences LW(m)

Figure 3

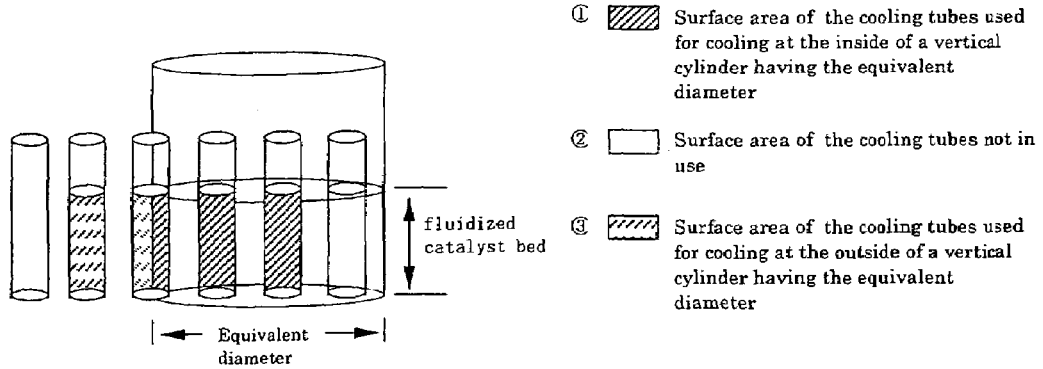

fluidized catalyst bed

Equivalent diameter

① ▨ Surface area of the cooling tubes used for cooling at the inside of a vertical cylinder having the equivalent diameter ② ☐ Surface area of the cooling tubes not in use ③ ▨ Surface area of the cooling tubes used for cooling at the outside of a vertical cylinder having the equivalent diameter S1; Total surface area of the cooling tubes existing in a vertical cylinder (having the diameter of the reactor) ①+②+③
S2; Surface area of the cooling tubes used for cooling at the inside of a vertical cylinder having the equivalent diameter ①

Horizontal section of the reactor

Horizontal section of the reactor

REACTOR FOR PRODUCING A NITRILE COMPOUND AND METHOD FOR OPERATING THE REACTOR

This application is a Divisional application of application Ser. No. 10/326,056, filed Dec. 23, 2002 now abandoned, the contents of which are incorporated herein by reference in their entirety.

BACKGROUND OF THE INVENTION

1. Field of the Invention

The present invention relates to a reactor for producing a carbon ring nitrile compound or a heterocyclic nitrile compound by ammoxidation of a carbon ring compound or a heterocyclic compound having organic substituents with ammonia and a gas containing oxygen in accordance with the gas phase reaction using a fluidized catalyst bed.

2. Description of the Related Arts

Carbon ring nitrile compounds are useful as raw materials for synthetic resins and agricultural chemicals and as intermediate compounds for amines and isocyanates. Heterocyclic nitrile compounds are useful as intermediate compounds for drugs, additives for feedstuffs and additives for foods.

The process of reacting an organic compound such as carbon ring compounds and heterocyclic compounds having organic substituents with ammonia and a gas containing oxygen is called ammoxidation and, in general, nitrile compounds are produced by a gas phase reaction using a fluidized catalyst.

It is known that catalysts containing vanadium, molybdenum or iron are used for the ammoxidation. For example, in Japanese Patent Application Laid-Open No. Heisei 11(1999)-209332, a process for ammoxidizing aromatic compounds and heterocyclic compounds having alkyl groups as substituents in the presence of a catalyst containing oxides of V, Cr, B and Mo is described. In Japanese Patent Application Laid-Open No. Heisei 9(1997)-71561, a process for producing dicyanobenzene by ammoxidation of xylene in the presence of a catalyst containing oxides of Fe, Sb and V is described.

As for the reactor of the gas phase reaction using a fluidized catalyst bed for ammoxidation, it is described in Japanese Patent Application Laid-Open No. Heisei 10(1998)-152463 that, in ammoxidation of methanol, a gas containing oxygen is introduced at a bottom portion of a vertical reactor, ammonia and a carbon ring compound is introduced at a side portion and the ranges of the density of the fluidized bed and the flow rates of the gases and the position of supply of the raw material are defined so that the contact between the gas of the raw material and the particles of the catalyst is improved.

It is described in Japanese Patent Application Laid-Open No. Heisei 10(1998)-120641 that, in a process for producing an aromatic nitrile by the gas phase ammoxidation, the position of the inlet of the raw material is decided in a manner such that, in the reaction zone, the ratio Wb/Wa of the amount by weight of the catalyst fluidized at the portion above the inlet for supplying the carbon ring compound (Wb) to the amount by weight of the catalyst fluidized at the portion above the inlet for supplying the gas containing oxygen (Wa) is in the range of 0.01 to 0.95. It is described that the yield and the selectivity of the aromatic nitrile of the object compound decrease when Wb/Wa exceeds 0.95.

In general, it is considered that the distribution of the temperature in the fluidized bed is kept approximately uniform when the fluidized condition within the bed is excellent. However, the distribution of the temperature is frequently not uniform when the reaction is a rapid exothermic reaction such as ammoxidation and a cooling tube is disposed for removal of heat. In particular, when the amount of heat generation per the unit volume of the fluidized bed (the density of heat generation) is great and the heat capacity of the catalyst particles is relatively small in comparison with the heat capacity of the gas phase, the distribution of the temperature is markedly uneven in an apparatus of the industrial scale having a fluidized bed and a column having a diameter exceeding 2 m. When the distribution of the temperature is uneven, drawbacks such as a decrease in the conversion and formation of byproducts arise at portions where the temperature is not optimum.

Moreover, with a reactor of the industrial scale having a fluidized bed and a column having a diameter exceeding 2 m. it is difficult that the uniform distribution of the temperature is achieved especially at the start of the operation, so it takes a long time to stabilize the temperature. As another problem, it is mentioned that the heat transfer efficiency of cooling tubes disposed in the reactor decreases when it operates for a long period time. Because of the problems mentioned above, it is difficult to achieve a stable and a long time operation.

SUMMARY OF THE INVENTION

The present invention has an object of providing, in the industrial production of a nitrile compound by ammoxidation using a gas phase reactor using a fluidized catalyst bed, a reactor which provides a uniform distribution of the temperature in the fluidized catalyst bed, enables the reaction to proceed in the optimum manner, easily stabilizes the temperature of the reaction and enables the continuous operation for a long time and providing a method for operating the reactor.

As the result of intensive studies by the present inventors to achieve the above object, it was found that the temperature of the reaction could be easily stabilized by using a cooling tube of the partial vaporization type and a cooling tube of the complete vaporization type in combination and the stable continuous operation could be achieved in an apparatus of the commercial scale, that the distribution of the temperature in the fluidized catalyst bed was made uniform by disposing the cooling tube in the fluidized catalyst bed in a specific arrangement and, moreover, that the stable continuous operation could be achieved for a long time by using water having a high purity as the cooling medium for the cooling tube of the complete vaporization type. The present invention has been completed based on the knowledge.

The present invention provides a reactor for producing a nitrile compound and a method for operating the reactor described in the following.

(A) A reactor for producing a nitrile compound from a carbon ring compound having organic substituents or a heterocyclic compound having organic substituents by a gas phase reaction using a fluidized catalyst bed with ammonia and a gas containing oxygen, the reactor comprising cooling tubes which are disposed in a cylindrical fluidized catalyst bed having a diameter of 2.0 meters or greater and comprise cooling tubes of a partial vaporization type in which a portion of a cooling medium is vaporized in the tubes and cooling tubes of a complete vaporization type in which an entire cooling medium is vaporized in the cooling tubes.

(B) A reactor described in (A), wherein an equivalent diameter defined by equation (1) in an arbitrary horizontal section of a region in the fluidized catalyst bed where the cooling tubes exist is in a range of 0.2 to 2.0 m and at least a portion of the cooling tubes exists in an arbitrary circle having a same diameter as the equivalent diameter and placed in the section, equation (1) being:

$$DE = 4 \times AF/LW \qquad (1)$$

wherein

DE(m): the equivalent diameter

AF(m$^2$): an area of a horizontal section of a flow route of the fluidized catalyst bed LW(m): a length of circumferences where the horizontal section of the flow route contacts the fluidized catalyst bed (a circumferential length of dipping).

(C) A reactor described in (B), wherein a ratio (S2/S1) of a surface area (S2) to a surface area (S1) of the cooling tubes is in a range of 0.01 to 0.30, wherein S1 represents an entire surface area of the cooling tubes existing in a vertical cylinder having, in an region in the fluidized catalyst bed where the cooling tubes exist, a bottom face as an arbitrary horizontal section of the region and an arbitrary height; and S2 represents a surface area of cooling tubes in use existing in a vertical cylinder having a bottom face as a circular section which is present in a same plane as that of the bottom face of the cylinder described for S1 and has a same diameter as the equivalent diameter and a same height as that of the cylinder described for S1.

(D) A method for operating a reactor for producing a nitrile compound which comprises using water having a concentration of ionic SiO$_2$ of 0.1 ppm or smaller and an electric conductivity of 5 µS/cm or smaller as a cooling medium supplied to a cooling tube of a complete vaporization type in the reactor for producing a nitrile compound described in (A).

BRIEF DESCRIPTION OF THE DRAWINGS

FIG. 2 shows a diagram describing the equivalent diameter DE in (B).

FIG. 3 shows a diagram describing the ratio (S2/S1) of the surface areas of cooling tubes in (C).

In FIG. 1, 1 means a reactor for producing a nitrile compound, 2 means a fluidized catalyst, 3 means an inlet for a gas containing oxygen, 4 means a disperser for the gas containing oxygen, 5 means an inlet for a carbon ring compound or a heterocyclic compound having organic substituents of the raw material and ammonia, 6 means a cooling tube, 7 means a cyclone for separating the catalyst, 8 means a tube for returning the catalyst, 9 means a tube for discharging the reaction gas and 10 means the surface of the fluidized catalyst bed.

DESCRIPTION OF THE PREFERRED EMBODIMENTS

Figure 1:
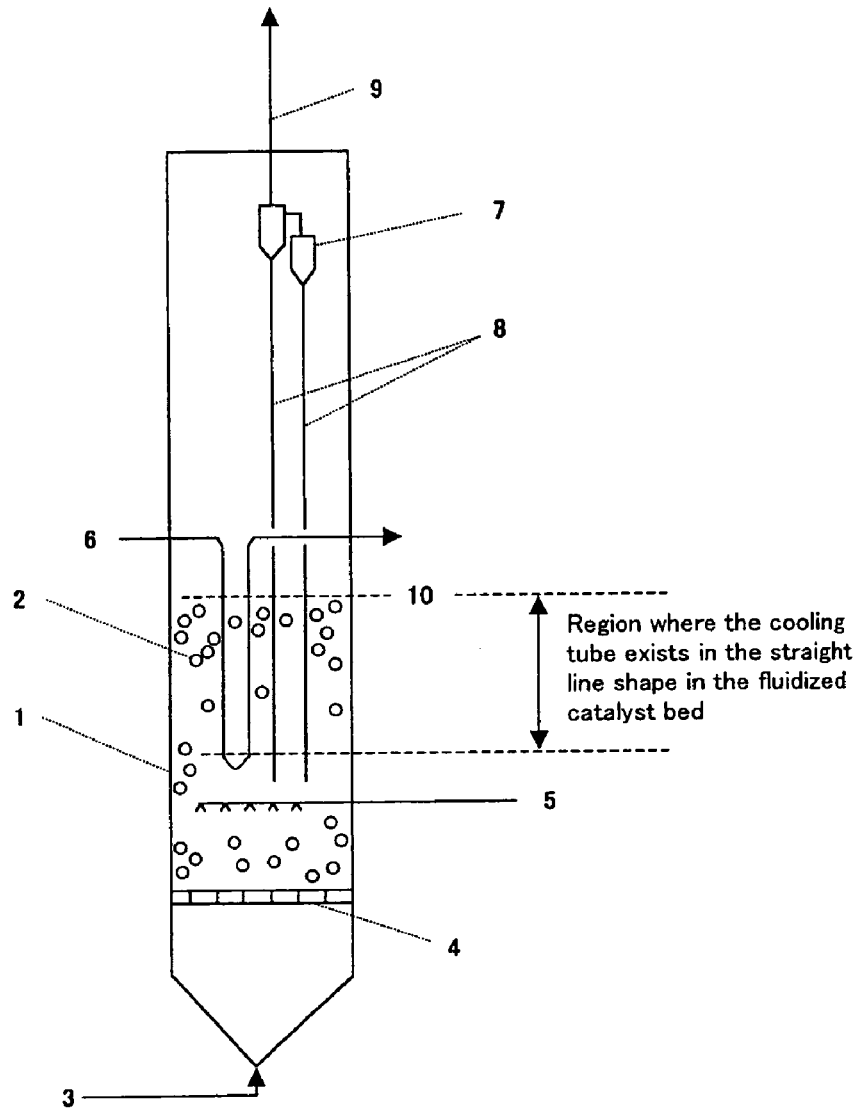
FIG. 1 shows a diagram describing an example of the structure of the reactor for producing a nitrile compound of the present invention.

FIG. 1 shows a diagram describing an example of the structure of the reactor for producing a nitrile compound of the present invention. In FIG. 1, a reactor of ammoxidation 1 is packed with a fluidized catalyst 2. A gas containing oxygen is introduced at a bottom portion 3 of the reactor and supplied to the reactor via a disperser 4. A carbon ring or heterocyclic compound having organic substituents of the raw material is supplied at a side portion 5 of a lower portion of the fluidized catalyst bed. A cooling tube 6 is disposed at the inside of the reactor. The surface 10 of the fluidized catalyst bed is placed at a lower portion of an upper portion of the cooling tube. Particles of the catalyst in a reaction gas are separated by a cyclone for the catalyst 7 and returned to the fluidized catalyst bed via a tube for returning the catalyst 8. The reaction gas from which the particles of the catalyst have been removed is discharged through the tube for discharging the reaction gas 9 at the top of the column. The reaction gas discharged at the top of the column which contained the unreacted carbon ring or heterocyclic compound, the nitrile compound, ammonia, hydrogen cyanide, carbon dioxide, water, carbon monoxide, nitrogen and oxygen is transferred to the next step and the nitrile compound is separated and purified.

The present invention relates to a reactor using a fluidized catalyst bed which has a column having a diameter of 2.0 m or greater and cooling tubes for removing heat of ammoxidation at the inside. The reactor is characterized by a specific arrangement of the cooling tubes at the inside of the fluidized catalyst bed and a specific manner of using the cooling tube.

In accordance with (A), a cooling tube of the partial vaporization type in which a portion of a cooling medium is vaporized in the tube and a cooling tube of a complete vaporization type in which an entire cooling medium is vaporized in the cooling tube are used in combination as the cooling tubes in the reactor using the fluidized catalyst bed and having a column having a diameter of 2.0 m or greater.

In general, the reaction using the fluidized catalyst bed is a form of reaction suitable for continuing the reaction while the heat generated by an intense exothermic reaction is rapidly removed. In the reactor, cooling tubes are disposed and the heat generated by the exothermic reaction is removed. As the type of the cooling tube for removing the heat, there are a cooling tube of the partial vaporization type in which a portion of a cooling medium is vaporized in the tube and a cooling tube of a complete vaporization type in which an entire cooling medium is vaporized in the cooling tube.

By the cooling tube of the partial vaporization type, a specific amount of heat corresponding to the area of heat transfer dipped into the fluidized catalyst bed is removed. On the other hand, by the cooling tube of the complete vaporization type, the amount of the removed heat varies depending on the amount of the medium supplied to the cooling tube.

In the method using the cooling tube of the partial vaporization type alone and controlling the amount of the removed heat by changing the number of the cooling tubes used among a plurality of disposed cooling tubes (changing the area of heat transfer) under a constant pressure of the generated vapor, the distribution of the temperature in the fluidized catalyst bed tends to be fluctuated in an operation not in the steady state such as the operations at the start and at the end and operations with changes in the load when the area of heat transfer per one cooling tube is great. The fluctuation in the distribution of the temperature can be decreased by increasing the number of the cooling tube so that the area of heat transfer per one cooling tube is decreased. However, the apparatus becomes complicated and is disadvantageous from the standpoint of economy.

In the method using the cooling type of the partial vaporization type alone and controlling the amount of the removed heat by adjusting the pressure of the generated vapor to change the temperature of the cooling medium, the difference in the temperature between the cooling medium and the fluidized catalyst bed can be increased and the required area of heat transfer can be decreased when the apparatus is operated while the vapor pressure is controlled in a range of low pressure. Therefore, this method is advantageous from the standpoint of economy. However, this method has a drawback in that, since the temperature of the cooling tube is low, byproducts of the reaction having high boiling points are attached to the outer surface of the cooling tube and the ability of heat transfer is markedly decreased. On the other hand, when the pressure of the vapor is increased to decrease the difference in the temperature between the cooling medium and the fluidized catalyst bed, the required area of heat transfer increases and the productivity tends to decrease since the amount of the removed heat is insufficient.

On the other hand, when the cooling tube of the complete vaporization type is used, the amount of the removed heat can be precisely adjusted by controlling the amount of the supplied cooling water and a stable distribution of the temperature can be obtained even during an operation not in the steady state. However, when the reactor is a commercial reactor having a diameter of 2 m or greater and the type of the cooling tube is a widely used vertical cooling tube having the U-shape, non-volatile metal components such as silica, alkali metals and alkaline earth metals tend to be precipitated and accumulated at the lower portion of the U-shape. In general, it is impossible that the accumulated substances are blown over the vertical portion of the U-shape and removed during the operation. As the amount of the accumulated substances increases, the efficiency of heat transfer decreases and problems arise due to stress cracking. Thus, the operation for a long time becomes difficult.

In accordance with (A), the distribution of the temperature can be made uniform and the control of the temperature can be improved by using the cooling tube of a partial vaporization type in which a portion of a cooling medium is vaporized in the tube and the cooling tube of a complete vaporization type in which an entire cooling medium is vaporized in the cooling tube in combination as the cooling tubes disposed in the fluidized catalyst bed. When the cooling tube of the partial vaporization type alone is used, the amount of removed heat changes stepwise since the amount of removed heat cannot be changed gradually and the temperature inside the reactor tends to become unstable although the entire portions of the cooling tubes dipped into the fluidized catalyst bed are effective as the area of heat transfer for cooling. When the cooling tube of the complete vaporization type alone is used, the effective area of heat transfer for cooling is limited to the range from the inlet of cooling water to the portion of the complete vaporization within the entire portions of the cooling tubes dipped into the fluidized catalyst bed and the cooling becomes uneven although the amount of cooling can be changed continuously. When an increased number of the cooling tubes of the complete vaporization type are used to achieve the uniform cooling, the control system is complicated and is disadvantageous from the standpoint of the cost.

The arrangements and the relative numbers of the cooling tube of the partial vaporization type and the cooling tube of the complete vaporization type can be suitably selected in accordance with the condition of the operation. It is preferable that (the amount of heat removed by the cooling tube of the complete vaporization type)/(the amount of heat removed by the cooling tube of the partial vaporization type) is in the range of 0.05 to 0.95 and more preferably in the range of 0.3 to 0.95. Controllability of the temperature is improved by using the cooling tube of the partial vaporization type and the cooling tube of the complete vaporization type in combination.

As the cooling tube, there are a horizontal cooling tube and a vertical cooling tube. The horizontal cooling tube is not preferable due to abnormal reactions and vaporization caused by accumulation of the catalyst at an upper portion. In general, a vertical cooling tube having the U-shape is preferable.

As the cooling medium, various cooling media may be used as long as the media is vaporized at the temperature of the operation. It is industrially advantageous that water is used.

When the cooling tube of the complete vaporization type is used continuously, it is preferable that the concentration of ionic silica is the cooling medium is 0.1 ppm or smaller and more preferably 0.05 ppm in accordance with (D). It is also preferable that the electric conductivity of the cooling medium is 5 µS/cm or smaller and more preferably 3 µS/cm. Under the above conditions, the decrease in the efficiency of cooling due to accumulation of silica and fracture due to stress cracking can be prevented and the continuous stable operation of the cooling tube of the complete vaporization type can be achieved. When the concentration of ionic silica or the electric conductivity of the cooling medium exceeds the above range, it is difficult that the stable operation is conducted for a long time.

Figure 4:
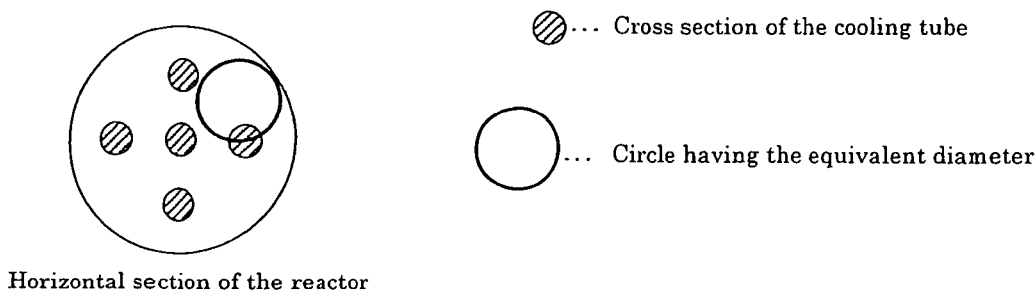
FIG. 4 shows a diagram exhibiting the arrangement of cooling tubes in (B) and (C).

In accordance with (B), it is preferable that an equivalent diameter defined by equation (1) in an arbitrary horizontal section of a region where the cooling tube exists in a straight line shape in the fluidized catalyst bed in the reactor for producing a nitrile compound (refer to FIG. 1) is in the range of 0.2 to 2.0 m and at least a portion of the cooling tube exists in an arbitrary circle having the same diameter as the equivalent diameter and placed in the section (refer to FIG. 4).

The equivalent diameter is represented by equation (1):

$$DE = 4 \times AF/LW \tag{1}$$

wherein

DE(m): the equivalent diameter

AF(m$^2$): an area of a horizontal section of a flow route of the fluidized catalyst bed LW(m): a length of a circumference where the horizontal section of the flow route contacts the fluidized catalyst bed (a circumferential length of dipping) (refer to FIG. 2).

In general, the equivalent diameter is related to the diameter of the formed bubble. When the equivalent diameter is smaller than 0.2 m, the diameter of the formed bubble is excessively small and the swelling of the bed is excessively great. Therefore, the size of the apparatus increases and the condition is disadvantageous. When the equivalent diameter exceeds 2.0 m, the diameter of the formed bubble is excessively great. Therefore, the efficiency of contact between the gas and the catalyst decreases and the condition is disadvantageous It is preferable that the ratio (S2/S1) of a surface area (S2) to a surface area (S1) of the cooling tubes is in the range of 0.01 to 0.30 and preferably in the range of 0.05 to 0.20 (refer to FIG. 3). The areas S1 and S2 are defined in the following:

S1 represents the entire surface area of the cooling tubes existing in a vertical cylinder having, in an region in the fluidized catalyst bed where the cooling tubes exist, a bottom face as an arbitrary horizontal section of the region and an arbitrary height; and S2 represents the surface area of cooling tubes in use existing in a vertical cylinder having a bottom face as a circular section which is present in the same plane as that of the bottom face of the cylinder described for S1 and has the same diameter as the equivalent diameter and the same height as that of the cylinder described for S1.

When a portion where (S2/S1) exceeds 0.30 exists, the area of cooling is excessively great in the portion and the distribution of the temperature in the fluidized catalyst bed cannot be made uniform. When a portion where (S2/S1) is smaller than 0.01 exists, the area of cooling tends to be insufficient in the portion and the distribution of the temperature in the fluidized catalyst bed cannot be made uniform. A ratio (S2/S1) may be controlled in the desired range by choosing a appropriate set cooling tubes out of all tubes.

The carbon ring compound having organic substituents which is used as the raw material for producing the nitrile compound in the present invention is a carbon ring compound having a carbon ring such as benzene ring, naphthalene ring, anthracene ring, cyclohexene ring, cyclohexane ring, dihydronaphthalene ring, tetraline ring and decaline ring and organic substituents such as methyl group, ethyl group, propyl group, formyl group, acetyl group, hydroxymethyl group, methoxycarbonyl group and alkoxyl group as the side chains on the carbon ring. The carbon ring compound may further have atoms and groups which do not take part in the ammoxidation such as a halogen group, hydroxyl group, amino group and nitro group. Examples of the carbon ring compound having organic substituents include toluene, xylene, trimethylbenzene, ethylbenzene, methylnaphthalene, dimethyl-naphthalene, methyltetraline, dimethyltetraline, chlorotoluene, dichloro-toluene, methylaniline, cresol and methylanisole.

The heterocyclic compound having organic substituents which is used as the raw material is a heterocyclic compound having a heterocyclic ring such as furan ring, pyrrol ring, indole ring, thiophene ring, pyrazole ring, imidazole ring, oxazole ring, pyran ring, pyridine ring, quinoline ring, isoquinoline ring, pyrroline ring, pyrrolidine ring, imidazoline ring, imidazolidine ring, piperidine ring and piperadine ring and organic substituents such as those described above as the side chains on the heterocyclic ling. Similarly to the above carbon ring compound, the heterocyclic compound may further comprise as the side chains thereof atoms and groups which do not take part in the ammoxidation such as those described above as the side chains. Examples of the heterocyclic compound include furfural, 2-methylthiophene, 3-methylthiophene, 2-formylthiophene, 4-methylthiazole, methylpyridine, dimethylpyridine, trimethylpyridine, methylquinoline, methylpyrazine, dimethylpyrazine and methylpiperadine. The above compounds may be used singly or as a mixture of two or more.

The catalyst used in the reactor of the present invention is not particularly limited as long as the catalyst is a catalyst of ammoxidation having the properties suitable for the gas phase reaction using a fluidized catalyst such as wear resistance. Preferable examples of the catalyst include fluidized catalysts comprising an oxide of at least one metal selected from vanadium (V), molybdenum (Mo) and iron (Fe).

The particle diameter of the entire catalyst is in the range of 10 to 300 μm. The average particle diameter is in the range of 30 to 200 μm and preferably in the range of 40 to 100 μm. The bulk density of the catalyst is in the range of 0.5 to 2 g/cm$^3$ and preferably in the range of 0.7 to 1.5 g/cm$^3$.

As the gas containing oxygen used for the ammoxidation, in general, the air is used. The air may be used after the content of oxygen is increased or may be used in combination with a diluent such as nitrogen gas and carbon dioxide gas. The amount of oxygen expressed as the ratio of the amount by mole of oxygen to the amount by mole of the organic substituent in the carbon ring or heterocyclic compound having organic substituents of the raw material ($O_2$/organic substituent) is 0.75 or more and preferably in the range of 1 to 25. When the amount of the air is less than the above range, the yield of the nitrile compound decreases. When the amount of the air exceeds the above range, the space-time yield decreases.

When ammoxidation is conducted using the air, the amount of the carbon ring or heterocyclic compound having organic substituents of the raw material based on the amount of the entire substances supplied to the reactor is in the range of 0.2 to 10% by volume and preferably in the range of 0.5 to 5% by volume, each amount being expressed as the volume of the gas. When the above amount is less than the above range, the yield of the nitrile compound decreases. When the above amount exceeds the above range, the space-time yield decreases.

In the present invention, ammonia of the industrial grade can be used as ammonia used for ammoxidation. The amount of ammonia expressed as the ratio of the amount by mole of ammonia to the amount by mole of the organic substituent in the carbon ring or heterocyclic compound is in the range of 1 to 10 and preferably in the range of 3 to 7. When the amount of ammonia is less than the above range, the yield of the nitrile compound decreases. When the amount of ammonia exceeds the above range, the space-time yield decreases.

The pressure of ammoxidation may be any of the atmospheric pressure, an added pressure and a reduced pressure. It is preferable that the pressure is in the range of around the atmospheric pressure to 0.2 MPa. The time of contact between the reaction gas and the catalyst is varied depending on the conditions such as the type of the carbon ring or heterocyclic compound having organic substituents of the raw material, amounts by mole of ammonia and the gas containing oxygen supplied for the reaction relative to the amount of the raw material and the temperature of the reaction. The time of contact is, in general, in the range of 0.5 to 30 seconds.

The temperature of the reaction is in the range of 300 to 500° C. and preferably in the range of 330 to 470° C. When the temperature is lower than the above range, the conversion decreases. When the temperature exceeds the above range, formation of byproducts such as carbon dioxide and hydrogen cyanide increases and the yield of the nitrile compound decreases. The temperature of the reaction is suitably decided so as to provide the optimum yield under the above conditions with consideration on the change in the activity of the catalyst.

In the reactor for producing a nitrile compound of the present invention, the temperature of the reaction can be stabilized by using the cooling tube of the partial vaporization type and the cooling tube of the complete vaporization type in combination in accordance with (A) and stable continuous operation can be conducted in the apparatus of the industrial scale; the distribution of the temperature can be made uniform by arranging the cooling tubes disposed in the fluidized catalyst bed in a manner such that the conditions described in (B) and (C) are satisfied; and the stable continuous operation for a long time is enabled by using the cooling medium described in (D) in the cooling tube of the complete vaporization type.

EXAMPLES

The present invention will be described more specifically with reference to Example and Comparative Example in the following. However, the present invention is not limited to Example and Comparative Example.

<Preparation of a Catalyst>

To 229 g of vanadium pentoxide $V_2O_5$, 500 ml of water was added. The resultant mixture was heated at 80 to 90° C. and 477 g of oxalic acid was added under sufficient stirring and dissolved. Separately, 400 ml of water was added to 963 g of oxalic acid and the resultant mixture was heated at 50 to 60° C. To the obtained solution, a solution obtained by adding 252 g of chromic acid anhydride $CrO_3$ into 200 ml of water was added under sufficient stirring and dissolved. To the solution of vanadium oxalate obtained above, the solution of chromium oxalate obtained above was mixed at 50 to 60° C. and a vanadium-chromium solution was obtained. To the obtained solution, a solution obtained by dissolving 41.1 g of phosphomolybdic acid $H_3(PMo_{12}O_{40})20H_2O$ into 100 ml of water was added. To the resultant solution, a solution obtained by dissolving 4.0 g of potassium acetate $CH_3COOK$ into 100 ml of water was added and, then, 2,500 g of a 20% by weight aqueous silica sol (containing 0.02% by weight of $Na_2O$) was added. To the obtained slurry, 78 g of boric acid $H_3BO_3$ was added and sufficiently mixed. The resultant fluid was concentrated by heating until the amount of the fluid became about 3,800 g. The obtained catalyst solution was dried by spraying while the temperature at the inlet was kept at 250° C. and the temperature at the outlet was kept at 130° C. The catalyst obtained after the drying by spraying was dried in a drier at 130° C. for 12 hours and calcined at 400° C. for 0.5 hours and, then, at 550° C. for 8 hours under a stream of the air and a fluidized catalyst was prepared. The catalyst contained the components in amounts such that the ratio by atom of the components V:Cr:B:Mo:P:Na:K was 1:1:0.5:0.086:0.007:0.009:0.020 and the concentration of the catalyst components in the fluidized catalyst was 50% by weight.

Example 1

The reaction was conducted using the reactor of ammoxidation shown in FIG. 1. The reactor for producing a nitrile compound was packed with the fluidized catalyst prepared above. After the air and meta-xylene (MX) were mixed with ammonia gas, the mixed gas was preheated at 180° C. and supplied to the reactor. The reaction was conducted under the following conditions: the concentration of MX: 2.8% by weight; the ratio of the amounts by mole of $NH_3/MX$: 6.8 ($CH_3$ group in $NH_3/MX$=3.4); the ratio of the amounts by mole of $O_2/MX$: 5.8 ($CH_3$ group in $O_2/MX$=2.9); SV: 456 $hr^{-1}$; and the pressure of the reaction: 0.08 MPa; and isophthalonitrile (IPN) was obtained.

The reactor for producing a nitrile compound had a column having a diameter of 2.5 m and the equivalent diameter obtained in accordance with equation (1) described above was 0.9 m. The cooling tubes were arranged in a manner such that, when a circle having the equivalent diameter is moved within the sectional plane of the fluidized catalyst bed, the cooling tubes always had a dipped circumference which is contained in or contacts this circle at any position of the circle (refer to FIG. 4). The ratio (S1)/(S2) of the sectional area of the cooling tubes existing within the circle having the equivalent diameter in the section of the fluidized catalyst bed (S2) to the sectional area of the entire cooling tubes in the fluidized catalyst bed (S1) was adjusted in a range of 0.1 to 0.16.

For the cooling, a coil of the partial vaporization type and a coil of the complete vaporization type were used. (the amount of heat removed by the cooling tube of the complete vaporization type)/(the amount of heat removed by the cooling tube of the partial vaporization type) is about 0.4. As the cooling water, water having an electric conductivity of 0.5 µS/cm and a concentration of ionic $SiO_2$ of 0.02 ppm was used.

When the operation was started, the load was gradually increased while the temperature of the reaction was monitored until the prescribed conditions were achieved. The temperature in the starting stage of the operation could be stabilized in about 3 hours after the supply of the raw material was started and in about 2 hours after the load of the raw material reached the prescribed value. The time required for the increase in the load of the raw material was about 1 hour.

Figure 5:
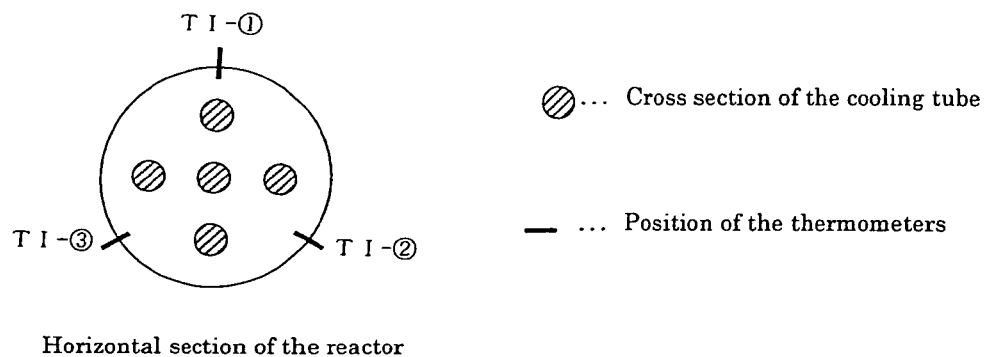
FIG. 5 shows a diagram exhibiting the arrangement of thermometers in Example 1 and Comparative Example 3.

The temperature was measured by thermometers disposed in three directions on the same plane in the reactor (refer to FIG. 5). The temperatures during the stable operation as expressed by the difference from the prescribed temperature of 420° C. were as follows:

TI-①: the prescribed temperature ±0° C.
TI-②: the prescribed temperature +5° C.
TI-③: the prescribed temperature −5° C.

In the above, the conversion of MX was 99% by mole and the yield of IPN was 83.9% by mole.

Comparative Example 1

Ammoxidation was conducted in accordance with the same procedures as those conducted in Example 1 except that the cooling tube of the partial vaporization type alone was used.

When the number of the used cooling tube of the partial vaporization type was increased in the starting stage of the operation, the cooling capacity increased stepwise. Due to the stepwise increase, marked fluctuations in the temperature of the reaction field took place several times during the period before reaching the constant load. The time required for the increase in the load was 2 hours after the supply of the raw material was started and was twice as long as that in Example 1. The time required for stabilizing the temperature after the load reached the prescribed value was about 3 hours and was 1.5 times as long as that in Example 1. The time required for stabilizing the temperature after the supply of the raw material was started was about 5 hours and was 1.7 times as long as that in Example 1.

Example 2

After the operation of the reactor was started and the temperature of the reaction was stabilized in accordance with the same procedures as those conducted in Example 1, the operation of the reactor was continued for a long time. The amount of heat removed by the cooling tube of the complete vaporization type was 6 tons/hr as expressed by the amount of generated steam. As the cooling medium, water having an electric conductivity of 0.5 μS/cm and a concentration of ionic $SiO_2$ of 0.02 ppm was used.

When the operation was continued for 10 months or longer, no decrease in the coefficient of heat transfer of the cooling tube or no leak of the cooling water into the process was found. When the inside was examined at the time of the regular repair after the operation was continued for about 330 days, no problems such as formation of cracks and pinholes were found in the cooling tube.

Comparative Example 2

The operation of the reactor was continued for a long time after the operation of the reactor was started and the temperature of the reaction was stabilized in accordance with the same procedures as those conducted in Example 1 except that water having an electric conductivity of 7 μS/cm and a concentration of ionic $SiO_2$ of 0.30 ppm was used as the cooling medium.

As the result of the continuous operation, a gradual decrease in the coefficient of heat transfer was found in about 2 months after the operation was started. In about 4 months after the operation was started, uneven distribution of the temperature in the horizontal direction inside the fluidized bed was found due to leak from the cooling tube. After about 5 months, the operation was stopped since the operation could not be continued any longer and the inside was examined. Cracks were found at the portion of the U-shape at the lower portion of the cooling tube.

Comparative Example 3

Ammoxidation was conducted in accordance with the same procedures as those conducted in Example 1 except that the cooling tube was used in a manner such that the maximum value of (S2/S1) was 0.4. The temperatures shown by the thermometers were as follows:

TI-①: the prescribed temperature ±0° C.
TI-②: the prescribed temperature −5° C.
TI-③: the prescribed temperature +15° C.

The conversion of MX was 99% by mole and the yield of IPN was 75% by mole.

What is claimed is:

1. A method for producing a nitrile compound, comprising reacting a carbon ring compound having organic substituents or a heterocyclic compound having organic substituents with ammonia and a gas containing oxygen, by a gas phase reaction using a fluidized bed catalyst, in a reactor comprising plural cooling tubes which are disposed in a cylindrical fluidized catalyst bed having a diameter of 2.0 meters or greater,
   (a) wherein said plural cooling tubes include (i) cooling tubes of a partial vaporization type in which a portion of a cooling medium is vaporized in the tubes and (ii) cooling tubes of a complete vaporization type in which an entire cooling medium is vaporized in the cooling tubes,
   (b) wherein an equivalent diameter defined by equation (1) in a horizontal section of a region in the fluidized catalyst bed where the cooling tubes exist is in a range of 0.2 to 2.0 m and at least a portion of the cooling tubes exists in a circle having a same diameter as the equivalent diameter and placed in the section, equation (1) being:

$$DE = 4 \times AF/LW \quad (1)$$

wherein
   DE (m): the equivalent diameter
   AF (m²): an area of a horizontal section of a flow route of the fluidized catalyst bed
   LW (m): a length of circumferences where the horizontal section of the flow route contacts the fluidized catalyst bed (a circumferential length of dipping), and
   (c) wherein a ratio (S2/S1) of a surface area (S2) to a surface area (S1) of the cooling tubes is in a range of 0.01 to 0.30, wherein
   S1 (m²) represents an entire surface area of the cooling tubes existing in a vertical cylinder having, in a region in the fluidized catalyst bed where the cooling tubes exist, a bottom face as a horizontal section of the region and a height; and
   S2 (m²) represents a surface area of cooling tubes in use existing in a vertical cylinder having a bottom face as a circular section which is present in a same plane as that of the bottom face of the cylinder described for S1 and has a same diameter as the equivalent diameter and a same height as that of the cylinder described for S1.

2. A method for producing a nitrile compound according to claim 1, wherein the cooling tubes are cooling tubes having a vertical U-shape.

3. A method for producing a nitrile compound according to claim 1, wherein the gas phase reaction using the fluidized catalyst bed is performed at a temperature in the range of 300° to 500° C., and wherein a cooling medium supplied to the cooling tubes of the complete vaporization type in the reactor is water having a concentration of ionic $SiO_2$ of 0.1 ppm or smaller and an electric conductivity of 5 μS/cm or smaller.

4. A method for producing a nitrile compound according to claim 1, wherein a ratio of amount of heat removed by the cooling tubes of the complete vaporization type to amount of heat removed by the cooling tubes of the partial vaporization type is in a range of 0.05 to 0.95.

5. A method for producing a nitrile compound according to claim 4, wherein said ratio of amount of heat removed is in a range of 0.3 to 0.95.

6. A method for producing a nitrile compound according to claim 2, wherein the gas phase reaction using the fluidized catalyst bed is performed at a temperature in the range of 300° to 500° C., and wherein a cooling medium supplied to the cooling tubes of the complete vaporization type in the reactor is water having a concentration of ionic $SiO_2$ of 0.1 ppm or smaller and an electric conductivity of 5 μS/cm or smaller.

* * * * *